United States Patent
Singh

(10) Patent No.: US 7,473,917 B2
(45) Date of Patent: Jan. 6, 2009

(54) LITHOGRAPHIC APPARATUS AND METHOD

(75) Inventor: Mandeep Singh, Delft (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 11/600,329

(22) Filed: Nov. 16, 2006

(65) Prior Publication Data

US 2007/0139646 A1    Jun. 21, 2007

Related U.S. Application Data

(63) Continuation-in-part of application No. 11/303,014, filed on Dec. 16, 2005.

(51) Int. Cl.
*G21K 5/00* (2006.01)
(52) U.S. Cl. .............................. 250/504 R; 250/493.1; 250/492.1
(58) Field of Classification Search ............ 250/504 R, 250/493.1, 492.1
See application file for complete search history.

(56) References Cited

U.S. PATENT DOCUMENTS

| | | | |
|---|---|---|---|
| 5,647,030 A * | 7/1997 | Jorgenson et al. ............. 385/12 |
| 5,929,981 A * | 7/1999 | Keilbach ..................... 356/73 |
| 6,067,154 A * | 5/2000 | Hossain et al. ........... 356/237.2 |
| 6,081,328 A * | 6/2000 | Eng ............................ 356/301 |
| 6,480,282 B1 | 11/2002 | Chinowsky et al. .......... 356/445 |
| 6,753,188 B2 * | 6/2004 | Perkins et al. ............... 436/172 |
| 6,784,999 B1 * | 8/2004 | Tao et al. ..................... 356/445 |
| 6,795,777 B1 * | 9/2004 | Scully et al. .................. 702/28 |
| 7,078,712 B2 * | 7/2006 | Perel et al. .............. 250/492.21 |
| 7,253,426 B2 * | 8/2007 | Gorrell et al. ................ 250/200 |
| 2003/0179379 A1 * | 9/2003 | Gedig ......................... 356/445 |
| 2005/0133727 A1 * | 6/2005 | Banine et al. ............... 250/397 |
| 2005/0148100 A1 * | 7/2005 | Su et al. ...................... 436/523 |
| 2005/0162657 A1 * | 7/2005 | Bahatt et al. ................. 356/445 |
| 2005/0170328 A1 * | 8/2005 | Gunnewijk et al. ............. 435/4 |
| 2005/0206892 A1 * | 9/2005 | Wang et al. .................. 356/301 |
| 2005/0244093 A1 * | 11/2005 | VanWiggeren et al. ........ 385/12 |
| 2006/0066859 A1 * | 3/2006 | Downey ...................... 356/445 |
| 2007/0139648 A1 | 6/2007 | Singh |
| 2007/0222996 A1 * | 9/2007 | Guan et al. .................. 356/445 |

OTHER PUBLICATIONS

Zhang, et al ("Surface plasmon detection of surface contamination on metallic film surfaces" Proceedings of SPIE vol. 777, 1987 p. 162).*
Homola, et al ("Surface plasmon sensors: review" Sensors and Actuators B 54(1999) 3-15).*
Hooper, et al ("Making tunnel barriers (including metals) transparent" Phys. Rev. Lett. 97, 053902 (2006)).*
Boussaad et al., "High-Resolution Multiwavelength Surface Plasmon Resonance Spectroscopy for Probing Conformational and Electronic Changes in Redox Proteins", Analytical Chemistry, vol. 72 No. 1, Jan. 1, 2000, p. 222.
Caruso et al., "Acousto-Optic Surface-Plasmon Resonance Measurements of Thin Films on Gold", J. Applied Physics, 83(2), Jan. 15, 1998, p. 1023.

(Continued)

*Primary Examiner*—David A. Vanore
*Assistant Examiner*—Michael Maskell
(74) *Attorney, Agent, or Firm*—Sterne, Kessler, Goldstein & Fox P.L.L.C.

(57) ABSTRACT

A lithographic apparatus is provided with a measurement apparatus constructed and arranged to use surface plasmon resonance to detect contamination of a surface within the lithographic apparatus.

30 Claims, 6 Drawing Sheets

OTHER PUBLICATIONS

Matsubara et al., "Optical Chemical Sensor Based on Surface Plasmon Measurement", Applied Optics, vol. 27, No. 6, Mar. 15, 1988, p. 1160.

Panigrahi et al., "Optical Surface Plasmon Resonance Sensor Design", Proceedings of SPIE, vol. 3897, Nov.-Dec. 1999, p. 534.

Kretschmann et al., "Radiative Decay of Non Radiative Surface Plasmons Excited by Light," (1968), pp. 2135-2136.

Homola et al., "Surface Plasmon Resonance Sensors: Review," Sensors and Actuators B 54 (1999), pp. 3-15.

Liedberg, et al., "Biosensing With Surface Plasmon Resonance—How It All Started," Biosensors & Bioelectronics 10 (1995), pp. i-ix.

Hooper et al., Making Tunnel Barriers (Including Metals) Transparent, Physical Revidw Letters, 97 (2006), pp. 053902-1-053902-4.

Otto, "Excitation of Nonradiative Surface Plasma Waves in Silver by the Method of Frustrated Total Reflection," Zeitschrift für Physik 216 (1968), pp. 398-410.

* cited by examiner

LITHOGRAPHIC APPARATUS AND METHOD

CROSS-REFERENCE TO RELATED APPLICATIONS

This application is a continuation-in-part of U.S. patent application Ser. No. 11/303,014, filed on Dec. 16, 2005 and currently pending, the entire content of which is hereby incorporated by reference.

FIELD

The present invention relates to a lithographic apparatus and a method for detecting contamination within a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

To be most effective, the lithographic apparatus is used in as clean an environment as possible. One of the main reasons for using a clean environment is to prevent contamination of the substrate and any optical surfaces which are used to manipulate radiation beams used to apply a desired pattern onto the substrate. For example, a lithographic apparatus using an extreme ultraviolet (EUV) radiation beam is known to generate contaminants which can lead to a deposit forming on the optical surfaces. For example, irradiation of some optical surfaces with EUV is known to cause the build up of a carbonaceous deposit on these optical surfaces. These deposits may reduce the operating resolution of the lithographic apparatus. It is thus desirable to minimize the contamination of optical surfaces and, when necessary, clean the surfaces to remove the deposits. Cleaning of the optical surfaces is undertaken when the level of the contaminant is such that the operation of the lithographic apparatus is compromised. Therefore, it is desirable to be able to detect the level of contaminants on the optical surfaces.

SUMMARY

The present invention provides a new apparatus and method for detecting the level of contamination on optical surfaces of a lithographic apparatus.

According to an aspect of the invention, there is provided a lithographic apparatus that is provided with a measurement apparatus constructed and arranged to use surface plasmon resonance to detect contamination of a surface within the lithographic apparatus.

According to an aspect of the invention, there is provided a method of detecting contamination within a lithographic apparatus, the method comprising using surface plasmon resonance to measure contamination of a surface within the lithographic apparatus.

According to an aspect of the invention, there is provided a method of detecting contamination within a lithographic apparatus, the method comprising measuring contamination of a surface within the lithographic apparatus using surface plasmon resonance.

According to an aspect of the invention, there is provided a lithographic apparatus provided with a measurement apparatus constructed and arranged to use tunneling of photons through a metal layer to detect contamination of a surface within the lithographic apparatus.

According to an aspect of the invention, there is provided a method of detecting contamination within a lithographic apparatus, the method comprising directing incident radiation at a metal layer, and detecting coupling of the incident radiation into a guided mode through the metal layer.

According to an aspect of the invention, there is provided a lithographic apparatus that includes a pattern device constructed and arranged to pattern radiation, a projection system constructed and arranged to project the patterned radiation onto a substrate; and a contamination detection system constructed and arranged to detect contamination of a surface within the lithographic apparatus using surface plasmon resonance.

According to an aspect of the invention, there is provided a method for manufacturing a device with a lithographic apparatus, the method comprising: patterning radiation with a patterning device; projecting the patterned radiation onto a substrate with a projection system; and detecting contamination of a surface within the lithographic apparatus using surface plasmon resonance.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 7b schematically depicts an embodiment of a prism of the contamination detection system of FIG. 7a; and FIG. 8 depicts an operating principle of the contamination detection system of FIG. 7a.

DETAILED DESCRIPTION

Figure 1:
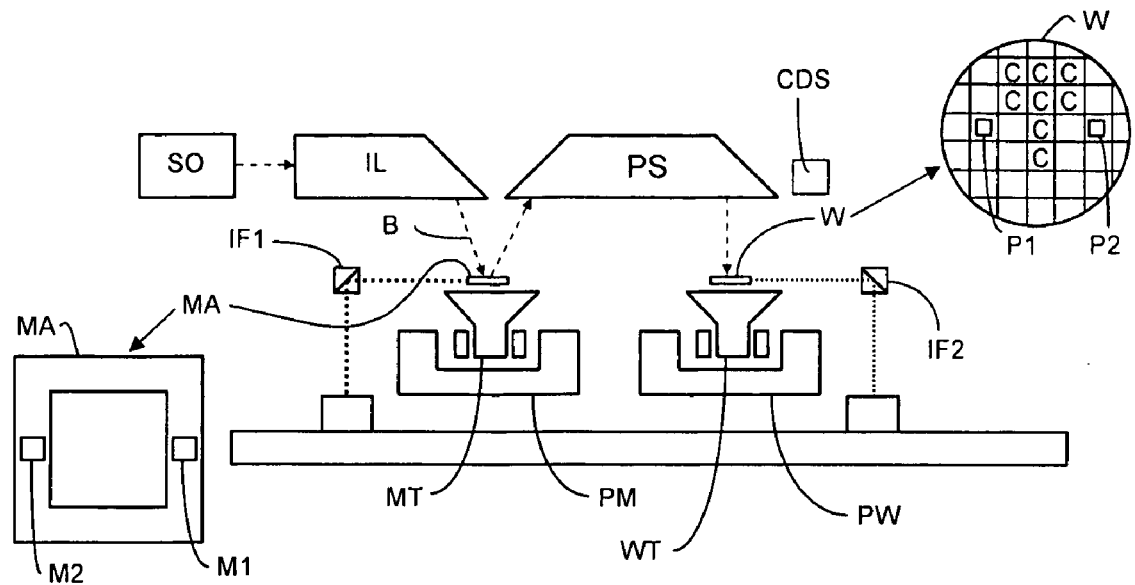
FIG. 1 schematically depicts a lithographic apparatus that includes a contamination detection system according to an embodiment of the present invention.

FIG. 1 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; a projection system (e.g. a refractive projection lens system) PS configured to project a pattern imparted to the radiation beam B by patterning device MA onto a target portion C (e.g. comprising one or more dies) of the substrate W; and a contamination detection system CDS configured to detect contamination of optical surfaces of the lithographic apparatus.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" as used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" as used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

It will be appreciated that the term "optical surfaces" used herein should be broadly interpreted as encompassing any surface that radiation is directed at, and in particular optical surfaces used in the conditioning, patterning and projection of the radiation beam B. For example, the optical surfaces may be mirrors, lenses or prisms. The optical surfaces may be transmissive or reflective. A reference optical surface may be one which receives stray light (i.e. an optical surface not in the path of the radiation beam B, but one which receives light reflected (for example) from other surfaces). Properties of the optical surfaces that radiation is directed at may be inferred from properties of the reference optical surface.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Contamination of optical surfaces is a problem in lithographic apparatus, and in particular, modern optical lithography, where diffraction-limited imaging is a prerequisite. This is particularly so in EUV lithography, where carbonaceous deposits will readily form under EUV illumination. The carbonaceous deposits arise because EUV that is incident upon certain optical surfaces (e.g. mirrors) causes electrons to be emitted from the optical surfaces. Typically, these electrons have an energy of between 5 and 50 eV. It is believed that these electrons crack hydrocarbons which are present in the (EUV) lithographic apparatus. These hydrocarbons are present despite the vacuum which exists in a lithographic apparatus, due to (for example) outgassing of components in the apparatus. Over time, these cracked hydrocarbons form a carbonaceous deposit on the optical surfaces of the lithographic apparatus.

It is desirable to detect the amount of carbonaceous deposits, because such deposits may reduce the effectiveness of the optical surfaces (e.g. mirrors) of the lithographic apparatus. For example, it has been found that for some lithographic apparatus, 2.0 nanometers is the maximum thickness of carbonaceous deposit that should be allowed to form on the optical surfaces, before the presence of the deposit is may compromise the operation of the apparatus. It is desired to be able to detect the absolute thickness of the contaminant with high resolution.

It has been proposed to use an ellipsometric apparatus to determine the level of contaminants on the optical surfaces. Ellipsometry is a sensitive optical technique that is able to determine the level of contamination using properties of elliptically polarized light reflected from the contaminated surface. The level of contamination may be determined by using a quarter-waveplate followed by an analyzer. The orientations of the quarter-waveplate and the analyzer may be varied until no light passes through the analyzer. From these orientations, the relative phase change of the light can be calculated, and from this, the level (or thickness) of the contamination of the optical surface can be determined. However, a disadvantage of ellipsometry is that it is difficult to use (especially in-situ), and the experimental results are also difficult to analyze. It is also difficult to achieve a high resolution measurement using ellipsometry.

An embodiment of the present invention uses surface plasmon resonance (SPR) spectroscopy to detect the level of contamination on optical surfaces of a lithographic apparatus. Surface plasmon resonance spectroscopy as a technique may be used to detect changes in the thickness of the contaminant by a fraction of a nanometer (e.g. 0.1 nanometers or less). Furthermore, and particularly advantageously, surface plasmon resonance spectroscopy may be undertaken in-situ, thereby allowing the level of contamination to be determined in real time without having to shut down the lithographic apparatus to perform contamination detection measurements. Being an optical technique, surface plasmon resonance has the advantage of being immune to electromagnetic field interference caused by any plasma formation and/or photoelectron emission caused by EUV radiation of optical surfaces.

Surface plasmon resonance is a non-destructive analysis technique. Surface plasmons are electron density oscillations formed at the surface of a conductor. Surface plasmons can be generated at the interface between a conductive metal film and an insulating layer by striking the metal layer with a particular type of light. A metal layer is used due to its large number of free electrons (i.e. its "sea" of electrons). The technique is often performed in a vacuum.

Surface plasmon modes may be resonantly excited in the metal layer by photons incident at a particular angle of incidence. This particular angle of incidence is mainly a characteristic of the optical constants of the materials used and the geometry of the surfaces. At a particular angle a photon incident on the metal layer will interact with a surface plasmon, and, rather than be reflected from the surface, will be coupled into the metal layer, causing a decaying evanescent field to propagate through the layer. Therefore, the interaction between the surface plasmon and the photon (excitation of the surface plasmon) results in a dip in the intensity of reflected light (specifically in the TM(p) polarized light, i.e. light with its electric field vector parallel to the plane of incidence) at a particular angle of incidence of the photons. This is observed as a dip in the angle-dependent reflectivity response of the metal layer, which is akin to a resonance at a particular angle.

As described above, properties of the surface plasmons and of the angles of incidence at which resonance occurs are highly dependent on the condition of the metallic surface, and therefore to any contamination deposited thereon. The reason for this is that the contamination of the metallic surface perturbs the decaying evanescent field at the vacuum-metal boundary, which in turn changes the angle at which surface plasmon resonance occurs. The evanescent field may be large at the boundary between the metal layer and the vacuum, leading to a high sensitivity to changes in thickness and/or refractive index of the contaminant at the interface. Thus, it will be appreciated that a measured change in the resonant angle can be used to determine the amount (or thickness) of contaminant on the metallic surface. Surface plasmon resonance spectroscopy is a technique disclosed in various publications, for example in B. Liedberg, C. Nylander and I. Lundstrom, "Biosensing with surface plasmon resonance—how it all started", Biosensors Bioelectron. 10, i-ix (1995) and J. Homola, S. S. Yee and G. Gauglitz, "Surface plasmon resonance sensors: review", Sensors and Actuators B, 54, 3-15 (1999). Therefore, mathematical details of the technique will not be described in more detail here.

Referring to FIG. 1, it can be seen that a contamination detection system CDS is positioned such that it is located away from (i.e. not in the path of) the radiation beam B, but is exposed to stray light which may be reflected from other surfaces in the lithographic apparatus. This means that the contamination detection system CDS does not obstruct or in any way intrude upon the patterning of the substrates, but is still able to measure the effect of irradiation by the radiation beam B, and therefore the build up of carbonaceous deposits on optical surfaces of the lithographic apparatus. The contamination detection system CDS uses surface plasmon resonance spectroscopy, described above, to determine the level of contamination.

Figure 2:
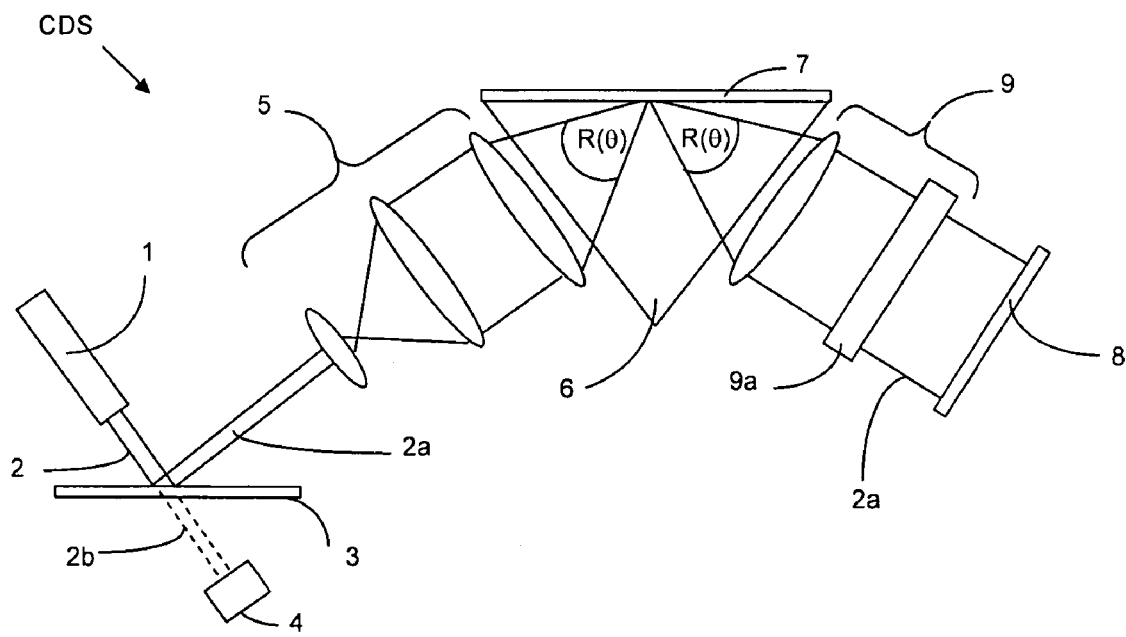
FIG. 2 schematically depicts the contamination detection system shown in FIG. 1 in more detail.

An embodiment of the contamination detection system CDS is shown in more detail in FIG. 2. The contamination detection system CDS is a surface plasmon measurement apparatus (e.g. a surface plasmon resonance spectrometer), and is provided with a radiation source 1 which is configured to provide a beam of radiation 2. The radiation beam 2 is directed towards a beam splitter 3, where it is split into two parts, a probing beam 2a and a reference beam 2b. The reference beam 2b is directed towards a detector 4. The intensity of the reference beam 2b is used as a reference level for the measurement of the thickness of the contaminant by the probing beam 2a.

The probing beam 2a is directed towards a beam expansion and focusing system 5. A polarizer (not shown) may be used to ensure the probing beam 2a has a specific polarization. The beam expanding and focusing system 5 first expands the probing beam 2a and then focuses the probing beam 2a, such that the probing beam 2a is made to pass through a prism 6 before focusing on a surface of the prism, upon which a metallic layer 7 has been deposited. The probing beam 2a is then reflected from the interface between the prism 6 and the metallic layer 7 before it is collimated and directed towards a CCD line detector 8 by a collimation and focusing system 9. The collimation and focusing system comprises a cylindrical lens 9a, which focuses the probing beam 2a in one dimension only, such that the probing beam is elongate in a direction parallel to the length of the CCD line detector 8, but focused in a direction perpendicular to its length. The probing beam 2a is not focused in two dimensions, as this would render it difficult or impossible to extract angular information therefrom. It will be appreciated that the cylindrical lens 9a can be used to focus the probing beam 2a before or after it has reflected from the metallic layer 7.

In an embodiment, the radiation source 1 may be a HeNe laser, having a wavelength of 632.8 nanometers, the prism 6 may be formed from fused silica, and the metallic layer 7 may be a 50 nanometer thick silver layer (other thicknesses and/or metals may be used). It will be appreciated that the radiation source 1 and metallic layer 7 may be chosen such that they are particularly suited to one another. For example, it is desirable that any dip in the reflection from the metallic surface 7 is particularly sharp and deep (i.e. such that it has a high figure of merit). A gold layer may be a suitable metallic surface in some circumstances, providing a high figure of merit where infra-red radiation is used to irradiate the metallic surface 7. Furthermore, it may be preferable to ensure that the prism 6 and metallic layer 7 are as closely matched as possible to the optical surfaces which are being used to condition, pattern and project the radiation beam B. For example, an additional two nanometer film (e.g. Ru) may be grown on top of the metallic layer 7 to simulate the capping layer of an EUV mirror used in EUV optical lithographic apparatus. In this way, a more accurate determination of the build up of deposits on the optical surfaces may be obtained. The metallic layer 7 may be deposited on top of a stacked layer of films, or multilayer dielectric thin film stack. By using a stack of thin film layers, the line-width of the reflection dip may be decreased, and therefore the resolution of the measurement improved.

It can be seen in FIG. 2 that as the probing beam 2a has been expanded and focused onto the interface between the prism 6 and the metallic layer 7; radiation impinges on the interface at a range of angles R(θ). Since a range of incident angles R(θ) is used, there is also a corresponding range of reflected angles R(θ). By using a CCD line detector 8, the effect of build up of contamination on the surface of the metallic layer 7 can be profiled at a range of different incident angles simultaneously. This negates the need to rotate the light source or any of the optical equipment, to find the above-mentioned resonant angle at which point the photons are coupled into the metallic layer and there is a dip in the reflected radiation intensity.

Figure 3:
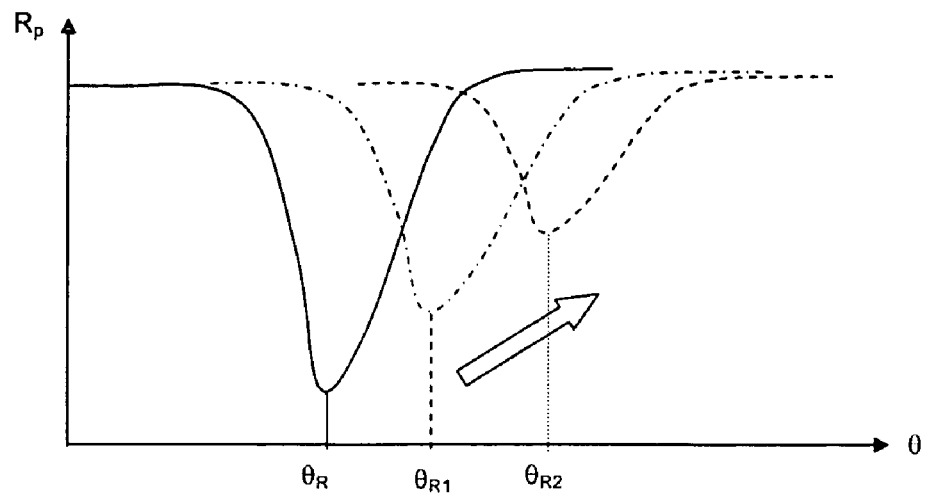
FIG. 3 depicts an operating principle of the contamination detection system of FIG. 2.

FIG. 3 illustrates how the apparatus of FIG. 2 is used. FIG. 3 is a graph of reflected intensity (specifically TM(p) polarization) verses angle of incidence of the probing beam 2a. It can be seen that there is a significant dip in the reflected intensity at an angle of incidence of $\theta_R$ which is the resonant angle for the prism 6 and metallic layer 7 combination. When a carbonaceous deposit forms on the metallic layer 7, the conditions required for surface plasmon resonance to occur are affected, such that the resonant angle changes. It can be seen from FIG. 3 that when the amount of contaminant increases to a first level, the resonant angle is shifted, and is now $\theta_{R1}$. A further increase in the thickness of the contamination layer further shifts the resonant angle to $\theta_{R2}$. Thus, using the CCD line detector 8, the shift in the resonant angle can be measured and subsequently used to derive the change in thickness of the contamination layer. The level of contamination can be determined experimentally, or calculated using known mathematical relationships (and using known optical constants of the contaminant). The use of beam expansion optics 5 and a CCD line detector 8 means that no parts of the contamination detection system CDS need to be moved during operation, thereby simplifying the operation of the apparatus.

Although FIG. 3 shows the dip in reflected intensity decreasing in depth as the resonant angle shifts, this is given by way of example only. The change in depth of the reflected intensity corresponds to more light being absorbed by an absorbent contaminant. If the contaminant is not absorptive, the depth of the intensity dip will not change (although a shift of the resonant angle will still occur).

Using surface plasmon resonance spectroscopy, the thickness of the contamination layer can be determined down to 0.1 nanometers or less, and with a resolution of much less than 0.1 nanometers.

In practice, the determination of the level of contamination may be undertaken periodically or continuously. When the deposit has been determined to exceed the desired maximum amount (for example 2.0 nanometers), atomic hydrogen (e.g. Hydrogen-1 or its isotope Hydrogen-2 (deuterium)) may be pumped into the lithographic apparatus to clean the optical surfaces. During and/or after cleaning has taken place, the contamination detection system CDS can be used to determine the (now decreased) level of contamination on the optical surfaces. When the optical surfaces have returned to their original state, this will be detected by the contamination detection system CDS from the resonant angle of the prism 6 and metallic layer 7 combination.

Since the level of contamination can be determined to a high resolution, cleaning of the optical surfaces can be undertaken at specific intervals, and need not be undertaken unnecessarily. If cleaning is undertaken too frequently, the optical surfaces themselves may become damaged. For example, excessive cleaning may remove or otherwise damage some or all of a reflective coating on an optical surface. Excessive cleaning of the optical surfaces may also have a detrimental impact on various construction materials in the lithographic apparatus.

The above-mentioned embodiment has been described with reference to the use of a beam expansion and focusing system 5 which is used to irradiate the interface between the prism 6 and metallic layer 7 with radiation at a range of angles $R(\theta)$. It will be appreciated however that the beam expansion and focusing system 5 is not necessary, and the radiation source 1 (or other radiation manipulation device) may instead be rotated with respect to the prism to vary the angle of incident radiation.

Instead of varying the angle of incidence of the probing beam 2a (or using a probing beam with a range of angles $R(\theta)$), the wavelength of the probing beam may be altered. This allows the angle of incidence of the probing beam 2a to be fixed at a single value. In this case, the wavelength of incident radiation is varied and a spectrum of the reflectivity as a function of wavelength is recorded. The spectral position of the reflection minimum may then be determined. The wavelength at which this minimum occurs will vary according to the amount of contaminant deposited on the metallic layer 7. In this way, the thickness of the layer of contaminant on the metallic layer 7 may be determined from the change in wavelength at which the dip in reflected radiation intensity occurs.

The wavelength may be altered by using a tuneable laser as the radiation source 1, or a broadband source with a monochromator or other optical wavelength resolving device at the detection side of the system. The wavelength resolving device may comprise a dispersive (grating or prism) monochromator, a Fourier transform spectrometer, a Fabry-Perot spectrometer, or a fiber-optic analogue of these.

The probing beam 2a could be generated by a diffuse or divergent source of radiation. The radiation source 1 may emit a specific wavelength of radiation, or a range of wavelengths. The radiation source 1 may incorporate one or more optical elements to control properties (e.g. the wavelength, polarization state, etc) of the probing beam 2.

Figure 4:
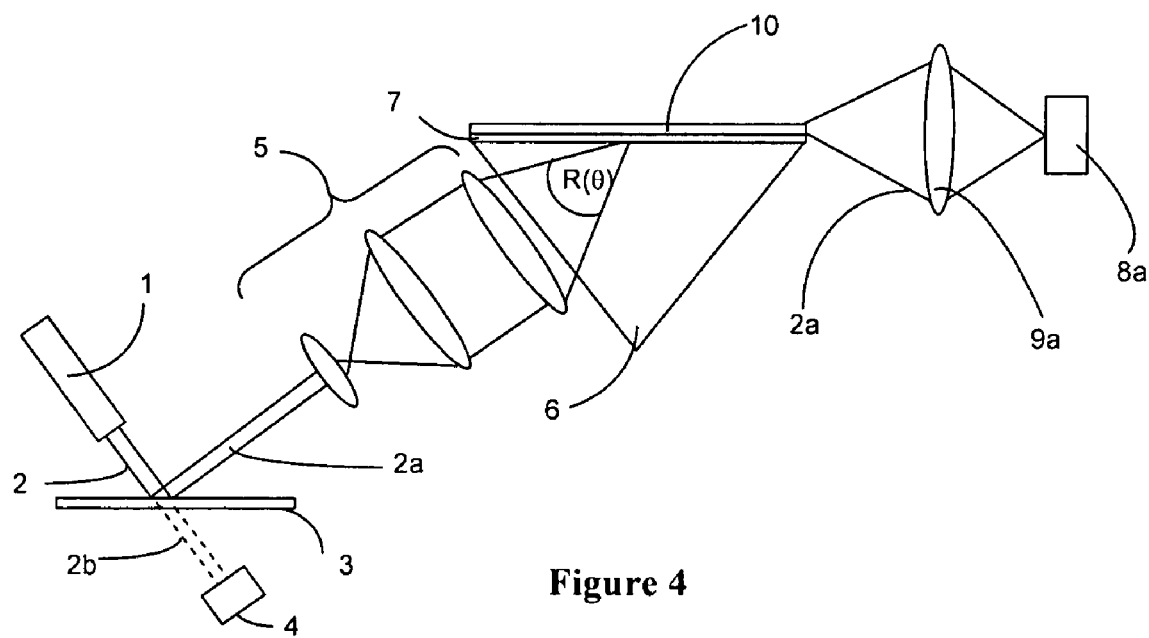
FIG. 4 schematically depicts another embodiment of the contamination detection system.

FIG. 4 illustrates another embodiment of the contamination detection system of the present invention. The contamination detection system shown in FIG. 4 is similar to that shown in FIG. 2, and common features have been given the same reference numbers. The contamination detection system comprises a radiation source 1 which is arranged to direct a beam of radiation 2 towards a beam splitter 3. The beam splitter is arranged to split the beam of radiation 2 into a reference beam 2b (which is used as a reference level for the measurement of the thickness of the contaminant) and a probing beam 2a. The reference beam 2b is directed toward a detector 4. The probing beam 2a is directed towards a beam expansion and focusing system 5. A polarizer (not shown) may be used to ensure that probing beam 2a has a specific polarization. The beam expanding and focusing system 5 first expands the probing beam 2a and then focuses the probing beam 2a, such that the probing beam 2a is made to pass through a prism 6 before focusing on a surface of the prism upon which a metallic layer 7 has been deposited.

In the contamination detection system of FIG. 2, the light reflected from the metallic layer 7 is detected. However, the apparatus shown in FIG. 4 differs in that a dielectric layer (e.g. silica) is deposited on top of the metallic layer 7, forming a waveguide 10. The waveguide 10 may be planar or have a ribbed structure. The probing beam 2a couples into the waveguide 10, and propagates along the waveguide 10 as a TE(s) polarized guided mode. The guided mode has a decaying evanescent field which extends outside of the waveguide (e.g. into the vacuum or other environment). Light propagating through the waveguide 10 is directed towards a detector 8a by a lens 9a.

Contamination forming on the surface of the waveguide 10 will cause a change in the effective index of the waveguide 10. The metallic layer acts as an optical tunnel barrier with the dielectric on either side (i.e. the prism 6 and waveguide 10) acting as "wells". The electric field tunnels through the barrier (metal) layer and launches a guided mode in the waveguide 10. The electric field leaks out of the waveguide 10 and decays evanescently. This decaying field is highly sensitive to the surface conditions, and therefore to any contamination layer which changes the effective index of the waveguide 10, thus altering its phase and spectral response.

It may be desired to arrange the embodiment of FIG. 4 such that wavelength resolved measurements are possible. For example the radiation source 1 may be a tuneable laser (e.g. incident at a single angle rather than over a range of angles) and the detector 8a may be a photodiode. Alternatively, a broadband source may be used, and the detector 8a may comprise a spectrometer and photodiode.

The formation of contamination on the surface of the waveguide 10 will cause a change in the wavelength at which radiation is coupled to the guided mode. This change of wavelength will be detected by the detector 8a. The amount or level of contamination deposited on the surface of the waveguide 10 may be determined based on the wavelength change. This may be done directly using known optical constants of the contaminants, or from a process of trial and error or empirical studies.

An advantage of the embodiment shown in FIG. 4 is that the metallic layer 7 is protected from environmental attack by the waveguide 10. Additionally, the spectral line-width of the guided mode radiating through the waveguide 10 is sharper (i.e. spectrally purer) than the surface plasmon mode of the single metal layer, thus enabling a more accurate determination of the thickness of the contaminant deposit.

The waveguide 10 is located adjacent the metallic layer 7 (i.e. in contact with the metallic layer 7, or with a small gap in between (the Otto configuration)) so that surface plasmons are excited.

If the contaminant is absorbing, then detection without the use of a waveguide (i.e. as described with reference to FIG. 2) may provide a higher resolution measurement. This is because propagation of radiation along the waveguide 10 will lead to absorption of the radiation and a consequent broadening of the spectrum of the radiation. This will reduce the resolution of a measurement of the radiation spectrum.

It will be appreciated that the apparatus of FIGS. 2 and 4 could be combined such that the surface plasmon resonance mode (that described in relation to FIG. 2) and an optically guided mode (that described in relation to FIG. 4) may be detected simultaneously.

The wavelength of the probing beam 2a may be chosen such that its frequency is resonant with an electronic or local vibration mode frequency characteristic of the particular contaminant to be monitored (e.g. carbon), i.e. so that a certain contaminant will (partly) absorb the probing beam 2a. Using such a specific wavelength allows the chemical nature of the contaminant to be confirmed, as well the amount of it which is deposited on the optical surface.

Figure 5:
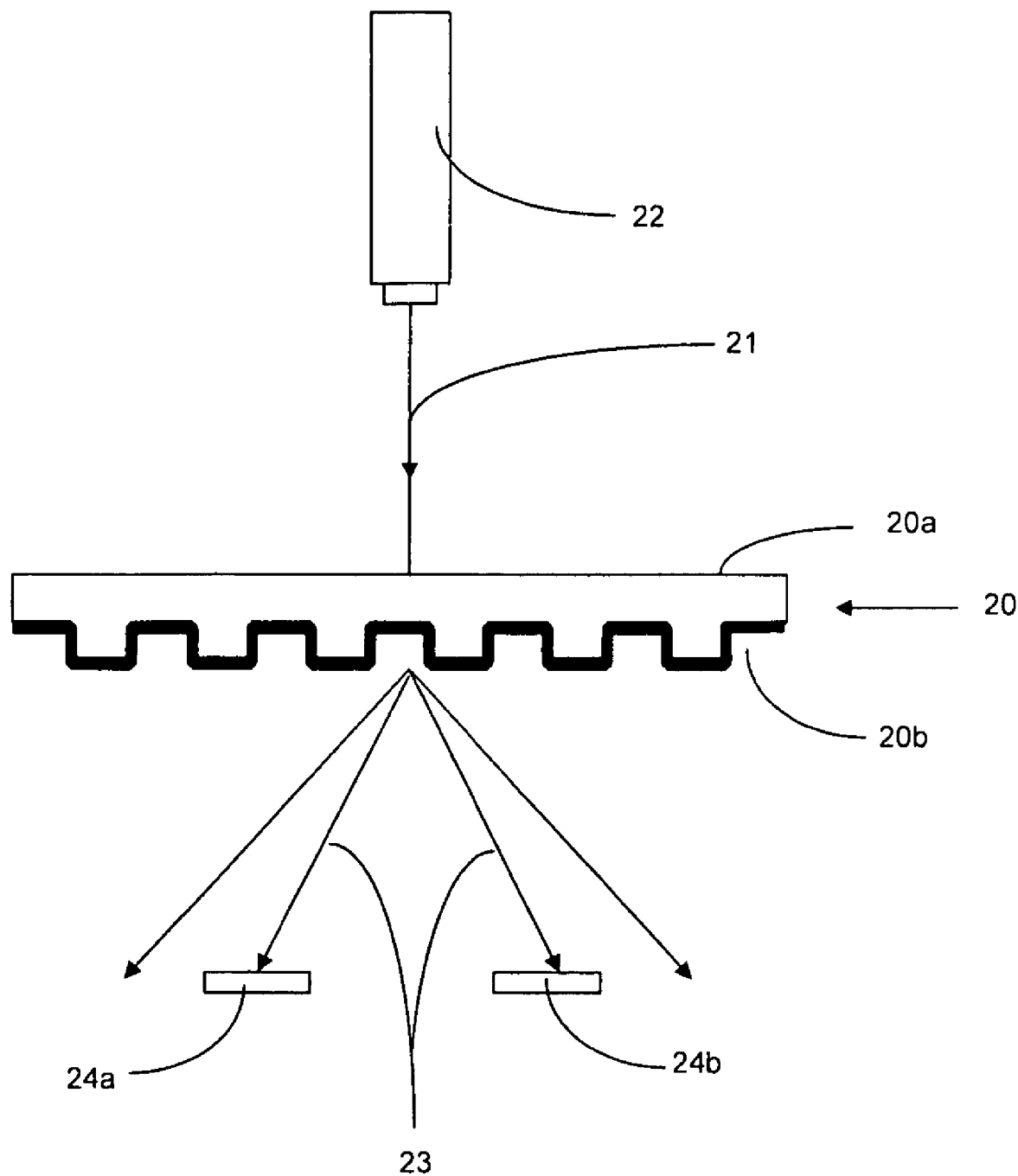
FIG. 5 schematically depicts another embodiment of the contamination detection system.

FIG. 5 illustrates another embodiment of the present invention (FIG. 5 is not shown to scale). In this embodiment, surface plasmon resonance spectroscopy is undertaken using a sub-wavelength grating structure 20. The grating comprises a metallic layer 20a provided on a glass substrate 20b (the grating having been etched into the glass substrate). A laser 22 directs a beam of radiation 21 towards the grating 20, such that incident radiation 21 is perpendicular to the surface of the grating 20.

The periodicity of the grating 20 serves to generate surface plasmon modes. The surface plasmon modes are generated when radiation is incident on the grating 20 from a perpendicular direction, avoiding the need to employ oblique incident radiation through a prism (as shown in FIGS. 2 and 4, which illustrate a Kretschmann geometry). Surface plasmon modes generated in the metal layer 20a cause a decaying evanescent field to be generated. The changes in the surface plasmon modes are detected, via detection of photons on the other side of the glass substrate 20b. Due to the periodicity of the grating 20, the photons are diffracted. First order diffracted photons 23 are detected by detectors 24a, 24b.

The wavelength of the incident radiation 21 is scanned across a range of wavelengths until a peak is detected in the intensity of the first order diffracted light 23. This peak corresponds to the conditions for surface plasmon resonance being met, and the position of the peak will shift when the thickness of the contaminant changes. Thus, when contamination (not shown) builds up on the grating 20, the wavelength at which surface plasmon resonance occurs will change. Therefore, by periodically irradiating the surface of the grating 20 and scanning the wavelength of the radiation, a change in the wavelength at which surface plasmon resonance occurs can be determined. From the shift of the wavelength required to generate surface plasmon resonance, the amount or level of contamination can be determined in a known manner.

It will be appreciated that instead of using a radiation beam 21 with a single wavelength, and then subsequently scanning the wavelength of this radiation beam 21, a broadband radiation source can be used. A spectrometer may then be used to detect light diffracted by the sub-wavelength grating structure 20 and to determine the wavelength peak at which surface plasmon resonance occurs. This peak will shift when the grating structure 20 becomes more or less contaminated.

When radiation of a single wavelength (i.e. monochromatic radiation) is used to irradiate the surface of the grating 20, a technique known as surface enhanced Raman spectroscopy may be used to detect the chemical nature of the contamination on the grating 20. If light scattered from the surface of the grating 20 has the same energy (i.e. wavelength) as that of the incident radiation 21, the incident radiation 21 will have been elastically scattered. However, if a shift in the wavelength (i.e. energy) of the scattered light is detected (in comparison with the incident radiation 21), the incident radiation 21 will have been inelastically scattered, i.e. some of the energy will have been absorbed by contamination on the surface of the grating 20. The change in the energy of the scattered light can be attributed to a characteristic property of the contamination, and therefore the chemical nature of the contamination can be determined. A change in wavelength or energy (the 'Raman shift') can be determined using a spectrometer such as a fiber coupled spectrometer, a compact grating spectrometer, a Fourier transform spectrometer, a Fabry-Perot spectrometer or any other suitable detection means.

The mechanism via which energy is absorbed by the contamination is as follows: the incident radiation 21 excites localized plasmons, which excite molecular dipoles. The molecular dipoles lose packets of energy to particular phonon vibrations. The molecular dipoles subsequently re-emit red-shifted (i.e. lower energy) photons. These photons, which have a lower energy than the photons of the incident radiation, are detected by the detectors 24.

Since the E-fields at the metal layer 20a are extremely high (due to surface plasmon coupling), the Raman signal may be enhanced by several orders of magnitude compared with what would ordinarily be seen. This is why the technique is called surface enhanced Raman spectroscopy. Although the embodiment of the invention shown in FIG. 5 uses a grating, other patterned surfaces may be used (typically a patterned surface that aids the conservation of momentum and hence surface plasmon coupling is used).

Figure 6:
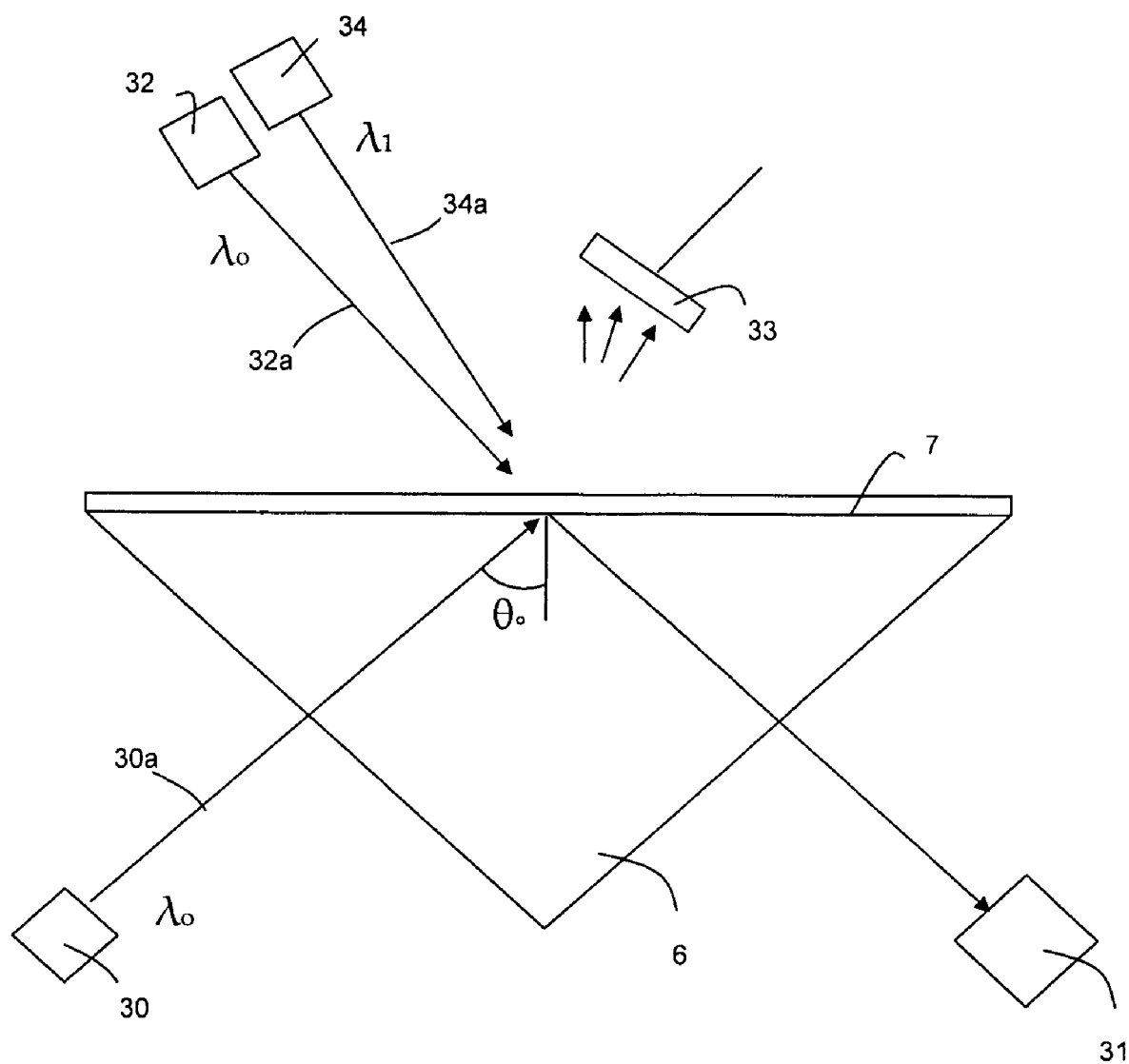
FIG. 6 schematically depicts another embodiment of the contamination detection system.

An alternative embodiment of the invention is shown in FIG. 6. A prism 6 is provided with a metallic layer 7. A tuneable laser 30 is arranged to direct a radiation beam 30a into the prism 6 such that it is incident upon the metallic layer 7 and reflected back out of the prism to a detector 31. The detector may for example be a photodiode. The wavelength of the tuneable laser is adjusted until surface plasmon resonance is excited at the metallic layer 7. This is seen as a drop in the intensity of radiation detected by the photodiode 31. The wavelength generated by the laser 30 is then fixed at this resonant wavelength $\lambda_o$. It will be appreciated that the resonant wavelength $\lambda_o$, is dependent upon the angle of incidence of the radiation on the metallic film 7. However, in this particular version of the embodiment this angle $\theta_0$ is fixed. In other versions the wavelength may for example be fixed and the angle may be varied. In a further alternative version a range of angles may be generated, for example using the configuration shown in FIGS. 2 and 4.

Since the metallic film 7 is being illuminated by radiation at an angle and wavelength which excites surface plasmon resonance, a significant number of plasmons will be present in the metallic film. A second tuneable laser 32 may be arranged to generate a second beam of radiation 32a having the same wavelength as that generated by the first tuneable laser 30, i.e. $\lambda_o$. This laser may be arranged to direct the second radiation beam 32a at an opposite side of the metallic film 7, i.e. without first passing through the prism 6. A detector 33 is positioned to detect radiation scattered from the metallic film 7. The detector 33 is wavelength resolving, and so can monitor the spectrum of the scattered radiation (the detector may for example be a spectrometer). The scattered radiation will include a range of wavelengths, which arise due to inelastic scattering of the radiation by any contamination upon the metallic film. The amount of this Raman scattered radiation is enhanced by the presence of the surface plasmons. Enhancing Raman scattering in this way is referred to as surface enhanced Raman spectroscopy. In some cases, the first beam of radiation 30a may be split into two beams, instead of using the second tuneable laser 32 to generate the second beam 32a.

A third laser 34 may be used to direct a third beam of radiation 34a with a different wavelength $\lambda_1$ at the metallic film 7. This third beam of radiation may be directed at the metallic film 7 without passing through the prism 6. The wavelength $\lambda_1$ is chosen to coincide with a peak of the Raman spectrum seen as a result of illuminating the metallic film 7 with the second radiation beam 32a. For example, the third radiation beam 34a may have a wavelength $\lambda_1$ which is selected to coincide with an electronic transition of a molecule present on the metallic film 7 (in the presence of excitation radiation at $\lambda_o$). In this embodiment, since the aim is to detect contamination on the metallic film 7, the wavelength of the third radiation beam 34a may be tuned to coincide with an electronic transition of the contamination. In this way it is the Raman spectrum of the contamination that is seen by the detector 33.

The effect of tuning the wavelength of the beam 34a generated by the third laser 34 is that the light is resonantly scattered. The effect of this is that vibrational and/or electronic modes associated with that particular transition exhibit a greatly increased Raman scattering intensity. Typically this increase is so high that it overwhelms Raman signals from all other transitions. For instance, resonance with a π-π* transition enhances stretching modes of the π-bonds involved with the transition, while the other modes remain unaffected. This "Resonance" Raman scattering is detected by the detector 33. Since the strength of the signal detected by the detector 33 is high, this allows accurate detection of a Raman spectrum of the contamination. This allows the nature of the contamination to be determined, i.e. which material or materials is present in the contamination. The thickness of the contamination may be determined by using the first laser 30 and detector 31 in a manner analogous to that described above in relation to FIG. 2 (i.e. using surface plasmon resonance measurements).

This embodiment of the invention may be used for example to pick out a particular contaminant when several contaminants are present. For example, the characteristic Raman spectrum for the contaminant to be detected may already be known, and the wavelengths $\lambda_o$ and $\lambda_1$ may be selected accordingly. In some instances, it may be the case that the Raman spectrum is known approximately, and experiments may be needed in order to more accurately determine the Raman spectrum. In one example, carbon deposited on the metal film 7 in an EUV environment may give rise to a particular characteristic Raman spectrum, which may be excited via appropriate selection of $\lambda_o$ and $\lambda_1$ For example, $\lambda_o$ may be 633 millimeters, and $\lambda_1$ could be 650 millimeters. In general, any suitable wavelength may be used, including infrared wavelengths such as 1.55 microns. Wavelengths which do not merely pass through the contamination will provide more Raman scattered radiation. When selecting $\lambda_o$ and $\lambda_1$ it should be kept in mind that in general Raman scattering is not particularly sensitive to the first wavelength $\lambda_o$. It is the difference between the first and second wavelengths ($\lambda_o - \lambda_1$) which should be selected to coincide with a peak of a Raman spectrum.

The radiation wavelengths $\lambda_o$ and $\lambda_1$ may be selected to excite the electronic Raman spectrum or the vibrational Raman spectrum. In some instances the vibrational Raman spectrum may be preferred for the detection of organic contamination (organic contamination will be seen in EUV lithography).

Figure 7A:
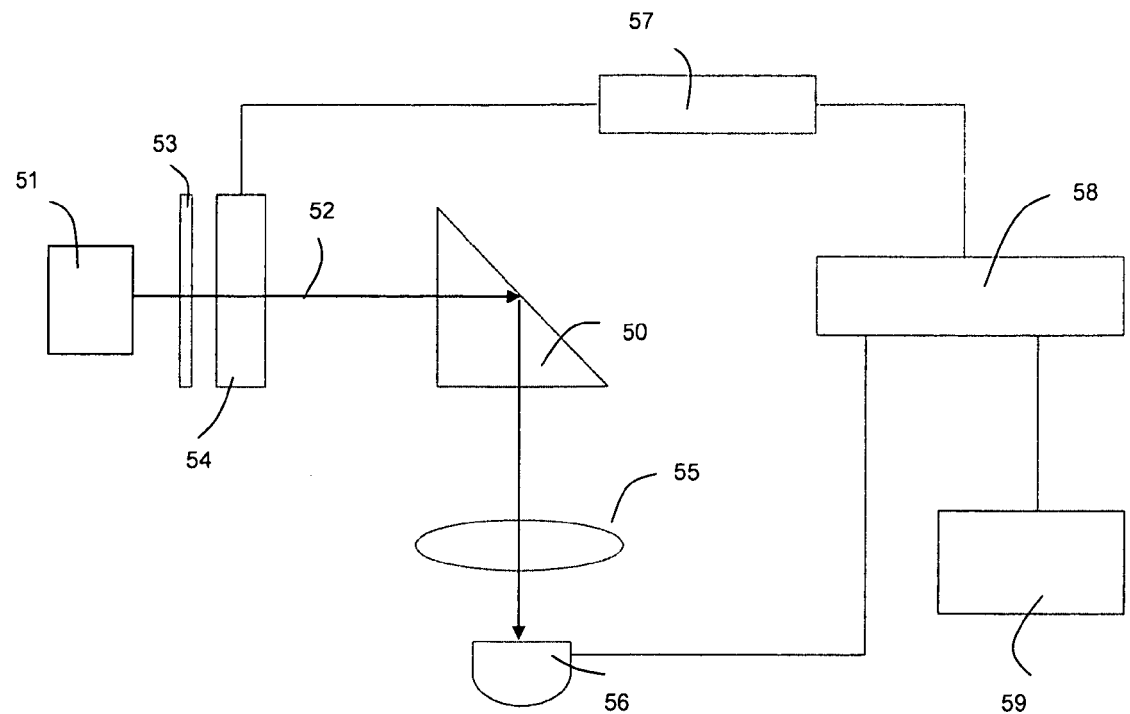
FIG. 7a schematically depicts another embodiment of the contamination detection system.

A further alternative embodiment of the invention is shown in FIG. 7a. In common with some of the above described embodiments, this embodiment is based around a prism 50. The prism 50 will be described in detail further below, in connection with FIG. 7b. A source 51 is arranged to generate a beam of radiation 52. The source may for example be a tuneable laser or a grating spectrometer. The radiation beam 52 passes through the polarizer 53 and a photo-elastic modulator 54 before passing into the prism 50. The radiation beam 52 is reflected from a surface of the prism, and passes through a lens 55 onto a detector 56. The detector 56 may for example be a photodiode. The photo-elastic modulator is controlled by a controller 57 with its reference frequency passed to a dual channel lock-in amplifier 58. An output from the lock-in amplifier 58 passes to a computer 59 or other data processing and/or storage apparatus.

Figure 7B:
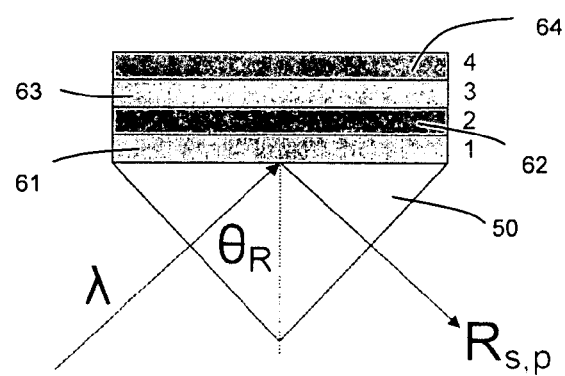

Referring to FIG. 7b, four layers are provided on the prism (the thickness of the layers is exaggerated in the figure). The first layer 61 is silver (Ag) with a thickness of 42 nanometers. The second layer 62 is Hafnia with a thickness of 292 nanometers (a quarter wave optical thickness of 2.0). The third layer 63 is silver (Ag) with a thickness of 42 nanometers. The fourth and final layer 64 is Alumina with a thickness of 24 nanometers (a quarter wave optical thickness of 0.13). The fourth layer 64 serves as a protective capping layer preventing the oxidation of the silver of the third layer. The materials and thicknesses are for a sensor operating in the near infrared region. Other thicknesses and/or materials may be used. For example other metals such as aluminium, gold or copper may be used in place of silver, depending upon in which spectral region the contamination detection system is arranged to operate. Similarly, other dielectric materials such as titania, silica, alkaline-earth fluorides and others may be used. The prism 50 is formed from BK7. Other prism materials may be used, for example, fused silica, glass (e.g. SF6, LaSFN9, etc) or crystal (e.g. Si, ZnS, ZnSe, SrTiO3, etc).

In use the polarizer 53 is arranged to ensure that the radiation beam 52 has a plane polarization. The photo-elastic modulator introduces a retardation into the radiation beam of up to λ/2 such that on leaving the photo-elastic modulator the radiation beam switches between orthogonal polarization states (i.e. between the s-plane and the p-plane polarization). The frequency at which the switching takes place is determined by the controller 57, and may typically be a few tens of kilohertz.

The combination of metal and dielectric layers 61-64 on prism allows 'optical tunneling' of photons through the layers, thereby allowing photons to interact with each of the layers, rather than only with the first silver layer 61. Optical tunneling is described in "Making Tunnel Barriers (Including Metals) Transparent", I. R. Hooper, T. W. Priest, J. R. Sambles, Phys. Rev. Lett., 97, 053902 (2006).

The interaction of the radiation beam 52 with the prism 50 (including the layers 61-64) is dependent upon the polarization state of the radiation beam. When the radiation beam is s-polarized there is no excitation of surface plasmons in the layers 61-64. Instead radiation is coupled, via optical tunneling into a waveguide mode which is centered on the Hafnia layer 62. The waveguide mode is confined because the first and third (silver) layers 61, 63 act as a form of Fabry-Perot cavity. As will be described further below, the angle at which the radiation beam 52 is directed at the prism is fixed, and the wavelength is varied. The coupling to the waveguide mode is wavelength dependent, and this coupling may be monitored using the detector 56.

When the radiation beam 52 is p-polarized, there is significant interaction between the radiation beam and plasmons present in the upper silver layer 63. Photons in the radiation beam reach the third (silver) layer 63 via optical tunneling through the first (silver) and second (Hafnia) layer. The first (silver) layer serves as a tunneling barrier for the p-polarized radiation.

The resonant frequency of the plasmon mode of the third (silver) layer 63 is strongly influenced by contamination on the fourth (Alumina) layer 64. This is because a surface wave is excited by E-field tunneling through the fourth (Alumina) layer 64. Since the resonant frequency of the plasmon mode of the third (silver) layer 63 is strongly influenced by the presence of contamination on the fourth (Alumina) layer 64, a measurement of the amount of contamination may be performed by monitoring the changes of the resonant frequency.

In use, the wavelength of the radiation beam is scanned, for example from 1100 nanometers to 1400 nanometers. The intensity of radiation incident upon the detector 56 is recorded as a function of wavelength. The lock-in amplifier 58 is used, together with the controller 57 to distinguish between detected p-polarized radiation and s-polarized radiation. The manner in which a lock-in amplifier and photo-elastic modulator may be used to distinguish between polarizations will be known to those skilled in the art and hence is not described in detail here. In brief however, the lock-in amplifier 58 is locked to the signal generated by the controller 57, thereby allowing the lock-in amplifier to distinguish between radiation detected when the photo-elastic modulator 54 is in a first state and radiation detected when the photo-elastic modulator is in a second state (i.e. to distinguish between s-polarized and p-polarized radiation). The use of the lock-in amplifier 58 in this way allows both s-polarized p-polarized spectral features to be observed simultaneously, and removes inaccuracies which would arise from drift and other time-based variations. It is not essential that a lock-in amplifier be used in order to discriminate between s-polarized and p-polarized radiation. For example, a polarizing beam splitter may be used to separate the polarizations and direct them towards different detectors. Other discriminating apparatus may be used.

If the lock-in amplifier (or other discriminating apparatus) and electro-optic modulator were not used, a set of measurements could be made for s-polarized radiation, followed by a set of measurements for p-polarized radiation (or vice-versa). However, this would be subject to drift and other time-based variations.

Figure 8:
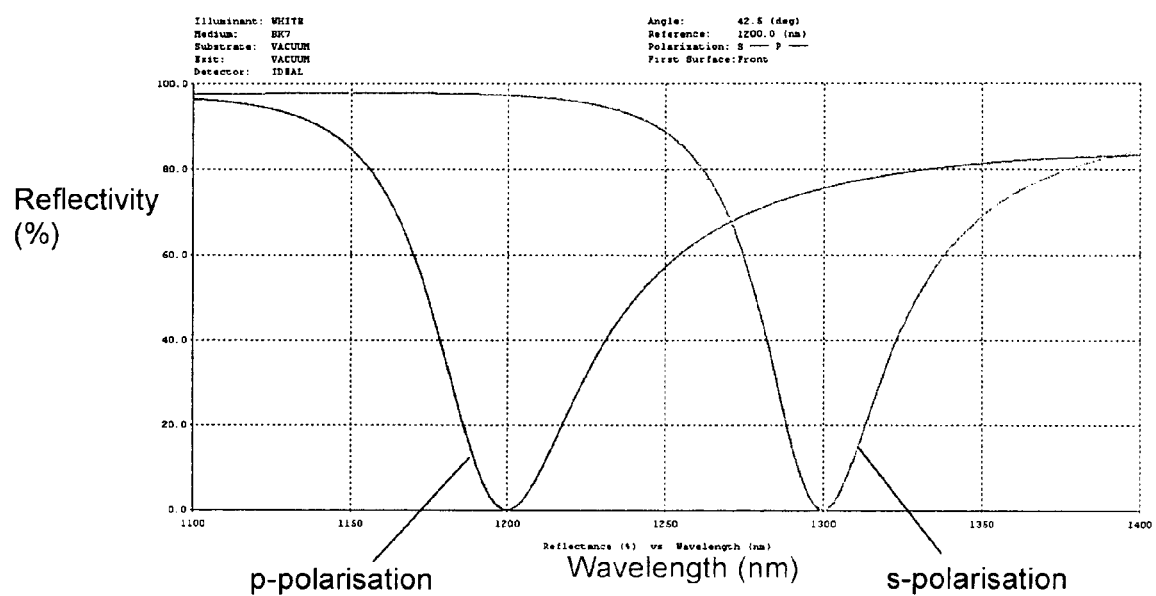

FIG. 8 shows the intensity detected by the photo detector 56 for both s-polarized and p-polarized radiation. The measurements have been normalized, and are represented as a percentage reflectivity of the prism 50. The p-polarized radiation can be seen to pass through a minimum of reflectivity at 1100 nanometers, before gradually rising to a reflectivity of around 83%. This characteristic arises from interaction of the p-polarized radiation beam 52 with surface plasmons in the third (silver) layer 63. Since the plasmons are sensitive to the presence of contamination on the fourth (Alumina) layer 64, the wavelength at which the minimum occurs will be shifted by the presence of contamination.

The s-polarized radiation passes through a minimum at 1300 nanometers, before rising to around 84%. This characteristic is due to coupling to the waveguide mode centered upon the second (Hafnia) layer. Since the waveguide mode is insensitive to the presence of contamination on the fourth (Alumina) layer 64, the wavelength of the minima is unaffected by the contamination.

The s-polarized radiation therefore provides a reference minimum against which the wavelength of the minima of the p-polarized radiation beam may be compared. By providing this reference, and using lock-in amplification to avoid a time delay between measurement of p-polarized radiation and s-polarized radiation, the embodiment of the invention provides an accurate measurement of contamination on the fourth (Alumina) layer 64.

In a variation of this embodiment, the source 51 may be a broadband source, and a Fourier transform spectrometer may be used to provide the radiation beam 52. A Fourier transform spectrometer is a Michelson interferometer with a moveable mirror. By scanning the moveable mirror over a distance, an interference pattern is produced which encodes the spectrum of the source. The embodiment of the invention operates in the same manner as described above, except that the measured intensities are recorded as a function of frequency rather than as a function of wavelength. A Fourier transform spectrometer may be used to generate a radiation beam for other embodiments of the invention.

In all of the above mentioned embodiments, sources and detectors of the contamination detection systems have been in close proximity to the optical surface that has been probed. Flowever, incident, reflected, scattered, diffracted, etc radiation may be introduced or collected using optical fibers. The use of fiber optics may allow parts of the contamination detection system to be located in places remote from an optical surface. For example, a spectrometer used to detect changes in wavelengths of reflected or diffracted radiation may be located outside of a lithographic apparatus, the reflected or diffracted radiation being passed to the spectrometer using fiber optic cables.

FIGS. 2, 4, 6 and 7 illustrate embodiments of the invention which utilize the Kretschmann geometry. The Otto configuration may alternatively be used. Details of the Kretschmann geometry and Otto configuration can be found in, for example, A. Otto, "Excitation of nonradiative surface plasma waves in silver by the method of frustrated total reflection," Z. Phys., 216, 398 (1968), and E. Kretschmann and H. Raether, "Radiative decay of nonradiative surface plasmons excited by light," Z. Naturforsch., 23A, 2135 (1968). Embodiments of the invention may alternatively utilize a grating coupling geometry, as illustrated in FIG. 5.

The embodiments of the invention may use a radiation beam with any suitable wavelength or range of wavelengths. Any suitable source may be used, for example a laser, diode, broadband source etc.

The embodiments of the invention shown in FIGS. 2 and 4 include a reference beam 2b which allows the intensity of the radiation incident on the prism 6 to be monitored. This same reference measurement arrangement, or some other equivalent arrangement, may be used for any of the embodiments of the invention.

The detection arrangement shown in FIG. 2, i.e. detecting radiation over a range of angles, may be used for other embodiments of the invention.

The embodiments of the invention have been described as being able to detect the chemical nature of the contamination of the optical surface. It will be appreciated that a binding agent may be deposited on an optical surface. This binding agent may be sensitive to (i.e. may bond with) particular chemicals. The binding agent may be chosen so that it binds to a particular contaminant. For example, the binding agent may be chosen such that long chain hydrocarbons bond with it. Where this is done, detected contamination on that optical surface may be assumed to be long chain hydrocarbon. The contamination detection system may for example be used to detect contamination of optical surfaces caused by a fluid that is used in immersion lithography. The fluid may be in contact with the optical surfaces or may provide gaseous contaminants (e.g. by evaporation).

The embodiments of the invention are suited for use in optical lithographic apparatus which use EUV radiation to expose substrates (the EUV radiation causes the build-up of carbonaceous deposits on optical surfaces in the lithographic apparatus). The embodiments of the invention may however be used to detect the level of contamination on optical surfaces in lithographic apparatus in general, i.e. not just contamination arising due to EUV radiation. Furthermore, the contamination need not necessarily be carbonaceous deposits or other inorganic materials. For example, the embodiments of the invention can be used to monitor the build up of biological or other organic material on optical surfaces. The contamination may consist of heavy hydrocarbons generated from vacuum and resist outgassing, and resist leaking into the fluid in immersion lithography.

It has been mentioned above that an example of a maximum level of contamination to be allowed on an optical surface may be 2 nanometers. It will be appreciated that this level is only an example, and that the maximum desired level may be higher or lower than 2 nanometers. Other factors which may be taken into account include the concentration of the contamination, the nature of the optical surface, and/or the nature or type of contamination.

As described above, the contamination detection system CDS is located such that it is exposed to stray radiation (the contamination detection system CDS is not located in the path of the radiation beam B used to expose the substrate). It will be appreciated that the contamination detection system CDS may be provided at one of a number of locations about the lithographic apparatus, and that this location may vary according to the exact layout of the lithographic apparatus and its constituent parts. Indeed, contamination detection systems may be provided at a plurality of locations within the lithographic apparatus. In some instances it may be possible to position a contamination detection system such that it detects contamination on a surface which is located in the path of the radiation beam B.

The form of the contamination detection system CDS (e.g. that of the prism 6 and metallic layer 7) of FIG. 2 may be such that it emulates the properties of optical surfaces used to condition, pattern and project the radiation beam B. In some cases, a single contamination detection system CDS may be sufficient for the purpose of determining the level of contamination of all optical surfaces in the lithographic apparatus in question. However, in other cases, in order to fully characterize the build up of deposits on a number of optical surfaces, it may be desirable to incorporate a plurality of contamination detection systems CDS. For example, each contamination detection system CDS may be constructed such that it has the same physical properties as a particular optical surface, and may be located as near to that optical surface as possible without interfering with the main radiation beam B.

Where a plurality of contamination detection systems CDS are used, in some cases some parts of the systems may be common. For example, a single tuneable source (or other radiation source) may be used to provide radiation for all of the contamination detection systems. This may be done by providing the single source remotely, and coupling the radiation to each measurement location using optical fibers. Similarly, a single detector may be used, for example linked to each measurement location using optical fibers. Multiplexing between measurement locations may be used. For example, where a single detector is used, multiplexing may be used to ensure that at any given time only radiation from one measurement location is incident upon the detector (the multiplexing providing switching between the measurement locations).

The surface plasmon measurement apparatus may be any apparatus suitable for detecting surface plasmons or the effects of surface plasmons. For example, the surface plasmon measurement apparatus may be a reflectometer arranged to detect light reflected from a surface, and/or the effect that surface plasmons have on this reflected light.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described.

The descriptions above are intended to be illustrative, not limiting. Thus, it will be apparent to one skilled in the art that modifications may be made to the invention as described without departing from the scope of the claims set out below.

What is claimed is:

1. A lithographic apparatus provided with a measurement apparatus constructed and arranged to use surface plasmon resonance to detect a thickness of contamination of a measurement surface within the lithographic apparatus, wherein the measurement surface is positioned such that the detected thickness of contamination of the measurement surface allows the thickness of contamination of an optical surface of the lithographic apparatus to be inferred.

2. The lithographic apparatus of claim 1, wherein the measurement apparatus is a surface plasmon resonance spectrometer.

3. The lithographic apparatus of claim 1, wherein the measurement apparatus is a surface enhanced Raman spectrometer.

4. The lithographic apparatus of claim 1, wherein the measurement apparatus is a surface enhanced resonance Raman spectrometer.

5. The lithographic apparatus of claim 1, wherein the measurement surface is provided on or adjacent to a prism.

6. The lithographic apparatus of claim 1, wherein a waveguide is provided at the measurement surface.

7. The lithographic apparatus of claim 2, wherein the measurement apparatus comprises a detector constructed and arranged to detect contamination of the measurement surface, and the measurement surface being one of a plurality of layers provided on a substrate, the plurality of layers including at least two metal layers and being capable of supporting a waveguide mode.

8. The lithographic apparatus of claim 7, wherein the measurement apparatus further comprises a polarization controller arranged to control the polarization of a radiation beam incident upon the measurement surface, and the plurality of layers are arranged such that s-polarized radiation couples to the waveguide mode and p-polarized radiation excites plasmons which have a resonance that is influenced by contamination on the measurement surface.

9. The lithographic apparatus of claim 8, wherein the polarization controller is a photo-electric modulator which is arranged to modulate the polarization, and the detector is connected to a discrimination apparatus which discriminates between the modulated polarizations.

10. The lithographic apparatus of claim 4, wherein the measurement apparatus comprises radiation sources arranged to emit radiation at first and second wavelengths, the difference between the wavelengths being selected to correspond to a peak of a Raman spectrum of the contamination, and a detector arranged to detect Raman scattered radiation.

11. The lithographic apparatus of claim 1, wherein the apparatus includes a radiation source comprising one of a broadband source or a single wavelength source or a tuneable source.

12. The lithographic apparatus of claim 11, wherein the radiation source includes a Fourier transform spectrometer.

13. The lithographic apparatus of claim 1, wherein the measurement surface forms part of the optical surface.

14. A method of detecting contamination within a lithographic apparatus, the method comprising:
    measuring a thickness of contamination of a measurement surface within the lithographic apparatus using surface plasmon resonance; and
    determining a thickness of contamination of an optical surface of the lithographic apparatus based on the measured thickness of contamination of the measurement surface.

15. The method of claim 14, wherein said measuring comprises monitoring a radiation wavelength or angle that resonantly excites surface plasmons, and wherein a shift in the wavelength or angle is indicative of contamination on the surface.

16. The method of claim 14, wherein said measuring comprises monitoring a spectrum of Raman scattered radiation from the surface to determine the presence or nature of contamination on the surface.

17. The method of claim 16, wherein the amount of Raman scattered radiation is enhanced by exciting transitions in the contamination, the transitions being excited by directing radiation at first and second wavelengths at the measurement surface, the difference between the wavelengths being selected to correspond to a peak of a Raman spectrum of the contamination.

18. The method of claim 14, wherein the surface being measured forms part of an optical surface.

19. The method of claim 18, wherein the surface being measured is provided on or adjacent to a prism.

20. A lithographic apparatus provided with a measurement apparatus constructed and arranged to use tunneling of photons through a metal layer to detect contamination of a surface within the lithographic apparatus.

21. The lithographic apparatus of claim 20, wherein the measurement apparatus is arranged to measure coupling of incident radiation into a guided mode.

22. The lithographic apparatus of claim 21, wherein the measurement apparatus is arranged such that the guided mode is on an opposite side of the metal layer from the location at which the incident radiation is incident on the metal layer.

23. The lithographic apparatus of claim 21, wherein the guided mode is centered on a waveguide, and wherein the waveguide is arranged such that during propagation of radiation along the waveguide, some of the radiation overlaps with the contaminated surface.

24. A method of detecting contamination on a contaminated surface within a lithographic apparatus, the method comprising:
    directing incident radiation at a metal layer; and
    detecting coupling of the incident radiation into a guided mode through the metal layer.

25. The method of claim 24, wherein the guided mode is centered on a waveguide, and wherein the waveguide is arranged such that during propagation of radiation along the waveguide, some of the radiation overlaps with the contaminated surface.

26. A lithographic apparatus comprising:
    a pattern device constructed and arranged to pattern radiation; a projection system constructed and arranged to project the patterned radiation onto a substrate; and
    a contamination detection system constructed and arranged to detect a thickness of contamination of a measurement surface using surface plasmon resonance,
    wherein the contamination detection system determines a thickness of contamination of an optical surface within the lithographic apparatus using the detected thickness of contamination of the measurement surface.

27. The lithographic apparatus of claim 26, wherein the contamination detection system comprises a surface plasmon resonance spectrometer.

28. The lithographic apparatus of claim 26, wherein the contamination detection system comprises a surface enhanced Raman spectrometer.

29. The lithographic apparatus of claim 26, wherein the contamination detection system comprises a surface enhanced resonance Raman spectrometer.

30. A method for manufacturing a device with a lithographic apparatus, the method comprising:
    patterning radiation with a patterning device;
    projecting the patterned radiation onto a substrate with a projection system;
    detecting a thickness of contamination of a measurement surface using surface plasmon resonance; and
    determining a thickness of contamination of an optical surface within the lithographic apparatus using the detected thickness of contamination of the measurement surface.

* * * * *